United States Patent
Robinson et al.

(10) Patent No.: US 9,536,718 B2
(45) Date of Patent: Jan. 3, 2017

(54) DETECTION OF MEMBRANE PROTEIN-THERAPEUTIC AGENT COMPLEXES BY MASS SPECTROMETRY

(75) Inventors: Carol V. Robinson, Oxford (GB); Sheila Wang, Oxford (GB); Nelson P. Barrera, Oxford (GB)

(73) Assignee: Oxford University Innovation Limited, Oxford (GB)

( * ) Notice: Subject to any disclaimer, the term of this patent is extended or adjusted under 35 U.S.C. 154(b) by 104 days.

(21) Appl. No.: 14/126,650

(22) PCT Filed: Jun. 18, 2012

(86) PCT No.: PCT/GB2012/051401
§ 371 (c)(1),
(2), (4) Date: Apr. 7, 2014

(87) PCT Pub. No.: WO2012/172378
PCT Pub. Date: Dec. 20, 2012

(65) Prior Publication Data
US 2014/0239169 A1  Aug. 28, 2014

(30) Foreign Application Priority Data
Jun. 17, 2011 (GB) .................................. 1110272.0

(51) Int. Cl.
*G01N 24/00* (2006.01)
*H01J 49/00* (2006.01)
(Continued)

(52) U.S. Cl.
CPC ....... *H01J 49/0027* (2013.01); *G01N 33/6848* (2013.01); *G01N 33/94* (2013.01);
(Continued)

(58) Field of Classification Search
CPC ............ G01N 33/6848; G01N 30/7266; G01N 33/6842; G01N 33/6851; G01N 2030/8831; G01N 2500/00; G01N 27/622; C12Q 2600/136; H01J 49/00; H01J 49/165; H01J 49/0418; H01J 49/0027; H01J 49/164
See application file for complete search history.

(56) References Cited

U.S. PATENT DOCUMENTS 6,287,857 B1   9/2001   O'Riordan et al.
6,790,632 B2   9/2004   Zweig
(Continued)

OTHER PUBLICATIONS

Laganowsky et al. "Mass spectrometry of intact membrane protein complexes", Nature Protocols, 2013, v. 8, No. 4, pp. 639-651.*
(Continued)

*Primary Examiner* — Yelena G Gakh
(74) *Attorney, Agent, or Firm* — Hodgson Russ LLP

(57) ABSTRACT

According to the present invention, there is provided a method of detecting a complex comprising a membrane protein bound to a therapeutic agent by mass spectrometry. The method comprises: (a) providing a solution comprising a detergent micelle in which said complex is contained; (b) providing a mass spectrometer comprising a nanoelectrospray ionization source, a mass analyzer and a detector; (c) vaporizing the solution using the nanoelectrospray ionization source under conditions such that the complex is released from the micelle; (d) ionizing the complex; (e) resolving the ionized complex using the mass analyzer; and (f) detecting the resolved complex using the detector. Also provided is a solution comprising a detergent micelle in which a complex is contained, wherein the complex comprises a membrane protein bound to a therapeutic agent.

21 Claims, 7 Drawing Sheets

(51) Int. Cl.
G01N 33/68 (2006.01)
G01N 33/94 (2006.01)
H01J 49/02 (2006.01)
B01D 15/38 (2006.01)

(52) U.S. Cl.
CPC .......... *H01J 49/02* (2013.01); *B01D 15/3842* (2013.01); *G01N 2333/705* (2013.01)

(56) References Cited

U.S. PATENT DOCUMENTS

| | | |
|---|---|---|
| 7,288,368 B2 | 10/2007 | Zweig |
| 7,575,763 B2 | 8/2009 | Sligar et al. |
| 7,592,008 B2 | 9/2009 | Sligar et al. |
| 7,595,155 B2 | 9/2009 | Murakami |
| 7,691,414 B2 | 4/2010 | Sligar et al. |
| 2002/0182717 A1 | 12/2002 | Karlsson |
| 2003/0219731 A1 | 11/2003 | Weinberger et al. |
| 2004/0033624 A1 | 2/2004 | Zweig |
| 2004/0259161 A1 | 12/2004 | Nilsson |
| 2005/0196791 A1 | 9/2005 | Koopman et al. |
| 2006/0019279 A1 | 1/2006 | Bosse et al. |
| 2007/0026383 A1 | 2/2007 | Trubetskoy et al. |
| 2007/0077291 A1 | 4/2007 | Petrenko |
| 2007/0249060 A1 | 10/2007 | Kirschner et al. |
| 2009/0117670 A1 | 5/2009 | Van Der Wijk et al. |
| 2009/0275066 A1 | 11/2009 | Popot et al. |
| 2010/0273677 A1 | 10/2010 | Lund-Johansen |

OTHER PUBLICATIONS

Hernandez & Robinson, Determining the stoichiometry and interactions of macromolecular assemblies from mass spectrometry, Nature Protocols, 2007, 715-726, vol. 2, No. 3.

Ho et al., Electrospray Ionisation Mass Spectrometry: Principles and Clinical Applications, Clin. Biochem. Rev., 2003, p. 3-12, vol. 24.

Sharon et al., Evidence for Micellar Structure in the Gas Phase, J. Am. Chem. Soc., 2007, 8740-8746, vol. 129, No. 28.

Chang et al., Structure of P-glycoprotein, Drug Metabolism Reviews: 9th Int'l Meeting of the Int'l Society for the Study of Xenobiotics (ISSX), 2010, 6-7, vol. 42, No. Suppl. 1.

Ilag, L.L., et al., Drug Binding Revealed by Tandem Mass Spectrometry of a Protein-Micelle Complex: supportive information, Journal of the American Chemical Society, Nov. 1, 2004, vol. 126, No. 44, pp. 14362-14363.

Barrera, N.P., et al., Mass spectrometry of membrane transporters reveals subunit stoichiometry and interactions, Nature Methods, Jul. 5, 2009, vol. 6, No. 8, pp. 585-587; http://www.nature.com/nmeth/journal/v6/n8/full/nmeth.1347.html#online-methods; & supplementary information.

Barrera, N.P., et al., Micelles Protect Membrane Complexes from Solution to Vacuum, Science, Jul. 11, 2008, vol. 321, No. 5886, pp. 243-246.

Wang, S.C., et al., Ion Mobility Mass Spectrometry of Two Tetrameric Membrane Protein Complexes Reveals Compact Structures and Differences in Stability and Packing, Journal of the American Chemical Society, Nov. 10, 2010, vol. 132, No. 44, pp. 15468-15470.

Barrera, N.P., et al., Advances in the Mass Spectrometry of Membrane Proteins: From Individual Proteins to Intact Complexes, Annual Review of Biochemistry, Jul. 7, 2011, vol. 80, No. 1, pp. 247-271.

Rakic-Martinez, et al., Listeria monocytogenes Strains Selected on Ciprofloxacin or the Disinfectant Benzalkonium Chloride Exhibit Reduced Susceptibility to Ciprofloxacin, Gentamicin, Benzalkonium Chloride, and Other Toxic Compounds, Applied and Environmental Microbiology, vol. 77, No. 24, pp. 8714-8721 Dec. 1, 2011.

* cited by examiner

DETECTION OF MEMBRANE PROTEIN-THERAPEUTIC AGENT COMPLEXES BY MASS SPECTROMETRY

FIELD OF THE INVENTION

The present invention relates to the detection of complexes comprising a membrane protein bound to a therapeutic agent. More particularly, the present invention relates to the detection of complexes comprising a membrane protein bound to a therapeutic agent by mass spectrometry.

BACKGROUND OF THE INVENTION

Membrane proteins are crucial in a wide range of biological functions including respiration, signal transduction and mediation of molecular traffic in and out of cells and organelles. In particular, membrane proteins play an important role in drug uptake and distribution and can therefore profoundly affect drug therapy and resistance to treatment by multiple drugs. By way of illustration, and without limitation, MDR1 P-glycoprotein (P-gp) is an ATP-driven low-specificity efflux pump playing a paramount role in the clearance of xenotoxins. This member of the ATPase Binding Cassette (ABC) transporters is a natural barrier against hydrophobic cytotoxic compounds, as well as natural products, cyclic and linear peptides. On the one hand, its overexpression in tumour cells, impairing targeted drug delivery, is a major pitfall for actual chemotherapies. On the other hand, recent studies have shown that gene therapies promoting the expression of MDR1 specifically in pluripotent hematopoietic stem cells could protect them from chemotherapeutics.

Despite their importance, membrane proteins and ligand-bound complexes thereof are notoriously difficult to study. X-ray crystallography is the standard technique for confirming the presence and position of ligands in the binding sites of membrane proteins. However, the conformational flexibility of a membrane protein or a membrane protein-ligand complex is restricted within a crystal lattice and may distort the structural and/or ligand-binding properties of a protein. Furthermore, difficulty is often encountered with the crystallisation of membrane proteins and membrane protein-ligand complexes.

Other methods for characterising membrane proteins and membrane protein-ligand complexes are also known, such as gel electrophoresis, analytical ultracentrifugation and X-ray scattering. However, these methods are low-resolution methods and usually require large quantities of protein. In addition, data from these methods do not normally reveal ligand binding to membrane proteins, or allow observation on post-translational modifications. In particular, the methods do not provide detailed information regarding drug binding to membrane proteins. Drug binding to proteins is often measured using indirect methods such as fluorescence or calorimetry. However, these methods do not provide structural or conformational information regarding the bound protein complex.

Until recently, mass spectrometry had not been considered suitable for detecting intact membrane proteins. This was primarily because of the insolubility of membrane proteins in buffers compatible with electrospray, as well as the ready dissociation of subunit interactions, both between transmembrane subunits and between transmembrane and cytoplasmic subunits, as a result of the transition of the protein into the gas phase environment of a mass spectrometer. However, the detection of a membrane protein, a membrane protein cooperatively bound to adenosine triphosphate (ATP) and a membrane protein bound with a lipid by electrospray ionisation-mass spectrometry has now been demonstrated (see Barrera et al, Science 2008, 321, 243-246; Barrera et al, Nat. Methods 2009, 6, 585-587; and Wang et al, J. Am. Chem. Soc. 2010, 132, 15468-15470). Despite these advances, the use of mass spectrometry to characterise the binding of membrane proteins to therapeutic agents such as drugs has not yet been demonstrated.

SUMMARY OF THE INVENTION

According to the present invention there is provided a method of detecting a complex comprising a membrane protein bound to a therapeutic agent by mass spectrometry, wherein the method comprises:
  (a) providing a solution comprising a detergent micelle in which said complex is contained;
  (b) providing a mass spectrometer comprising a nano-electrospray ionisation source, a mass analyser and a detector;
  (c) vaporising the solution using the nanoelectrospray ionisation source under conditions such that the complex is released from the micelle;
  (d) ionising the complex;
  (e) resolving the ionised complex using the mass analyser; and
  (f) detecting the resolved complex using the detector.

Also provided is a solution comprising a detergent micelle in which a complex is contained, wherein the complex comprises a membrane protein bound to a therapeutic agent.

A method of the present invention may be used to detect binding between a membrane protein and a therapeutic agent. In particular, a method of the present invention may allow one or more structural characteristics (e.g. stoichiometry) of the membrane protein-therapeutic agent complex to be determined, and/or may also be used to detect conformational changes that take place upon binding of the therapeutic agent to the membrane protein.

A method of the present invention may allow therapeutic agents to be screened. In contrast to indirect methods such as fluorescence or calorimetry, the present method may allow therapeutic agents to be screened directly. In particular, a method may be used to screen for the binding of activators and transporter substrates which are difficult to screen using conventional in vivo methodologies. Moreover, unlike X-ray crystallography, the present methods are not complicated by the inherent structural flexibility of membrane protein-therapeutic agent complexes and may allow the dynamical behaviour of membrane proteins and their interaction with therapeutic agents to be studied. In addition, a method of the present invention may use significantly less sample than other analytical methods.

DESCRIPTION OF VARIOUS EMBODIMENTS

Figure 1:
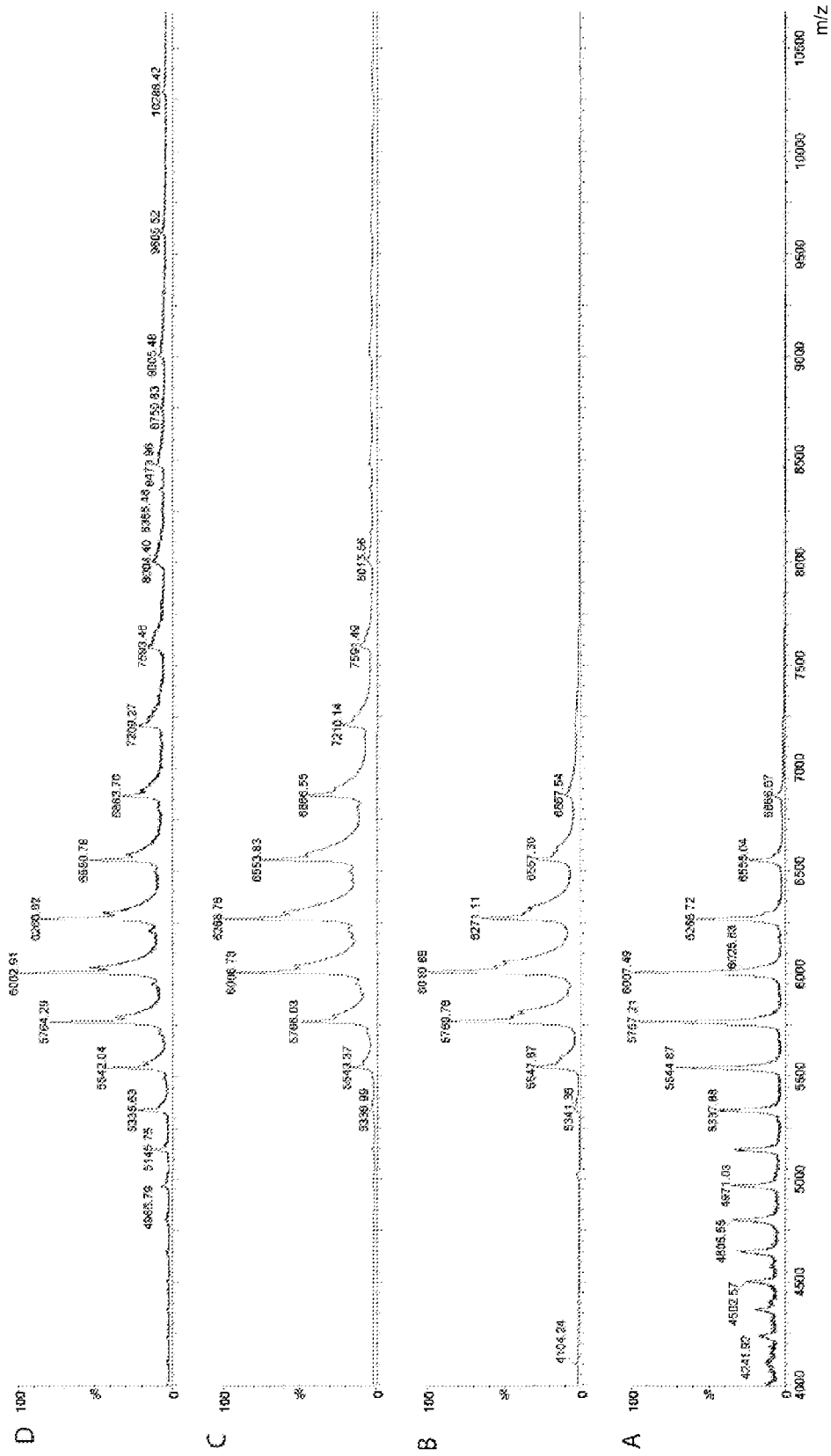
FIG. 1 shows mass spectra of: (A) apo-P-gP; (B) P-gp bound to the inhibitor QZ59Se, RRR; (C) P-gp bound to the inhibitor HT-35; and (D) P-gp bound to the activator HT-122.

According to the present invention, a complex comprising a membrane protein bound to a therapeutic agent is detected by mass spectrometry. A method of the present invention involves the use of a solution comprising a detergent micelle in which the complex is contained. The solution is vaporised using a nanoelectrospray ionisation source under conditions such that the complex is released from the detergent micelle. The complex is ionised, and subsequently resolved and detected.

Membrane proteins can be grouped into integral membrane proteins and peripheral membrane proteins. Integral membrane proteins may have one or more segments embedded within a membrane and may be bound to the lipid bilayer. Peripheral membrane proteins may be temporarily associated with the lipid bilayer and/or integral membrane proteins. In an embodiment, the membrane protein that forms part of the membrane protein-therapeutic agent complex is an integral membrane protein.

Membrane proteins may be composed of one (mono) or more (multi) associated polypeptide chains. Thus, the membrane protein may be a monomeric or a multimeric membrane protein, for example an oligomeric membrane protein. Oligomeric membrane proteins include both homooligomeric (identical polypeptide chains) and heterooligomeric (different polypeptide chains) proteins.

In an embodiment, the membrane protein is an integral membrane protein selected from G protein-coupled receptors (GPCRs), membrane transporters, membrane channels, ATP-binding cassette transporters (ABC-transporters) and proton driven transporters. In a particular embodiment, the membrane protein is selected from EmrE, LmrP, MscL, BtuCD, $BtuC_2D_2$, LmrCD, MacB, MexB, P-gp, MsbA, peptide transporters, NorM and KirBac3.1. In an embodiment, the membrane protein is P-gp.

In an embodiment, the membrane protein has a molecular weight of from about $10^3$ Daltons to about $10^{12}$ Daltons, e.g. from about $10^3$ Daltons to about $10^6$ Daltons.

Methods for the purification and expression of membrane proteins are known in the art. By way of example, Barrera et al, Nat. Methods 2009, 6, 585-587 describe methods for the purification of MacB, LmrCD, and EmrE. Moreover, Drew et al, Nat. Protoc. 2008, 3, 784-798 describe a GFP fusion construct methodology in which yields in the overexpression and purification of membrane proteins are improved, while Aller et al, Science, 2009, 323, 1718-1722 describe P-glycoprotein expression and purification.

The therapeutic agent may be an active compound which, when administered to an organism (human or non-human animal), induces a desired pharmacologic, immunogenic, and/or physiologic effect by local and/or systemic action. Examples of therapeutic agents include, without limitation, drugs, vaccines and biopharmaceutical agents. Thus, therapeutic agents may include small molecule drugs, therapeutic proteins, peptides and fragments thereof (whether naturally occurring, chemically synthesised or recombinantly produced), and nucleic acid molecules (including both double- and single-stranded molecules, gene constructs, expression vectors, antisense molecules and the like). Therapeutic agents may also include substrates, inhibitors, activators, neurotransmitters, agonists and antagonists. The therapeutic agent may be a synthetic or naturally occurring compound. The therapeutic agent may be a drug candidate or other agent suspected of having therapeutic application.

Particular examples of therapeutic agents include, but are not limited to, anti-cancer agents, anti-infective agents (e.g. antibiotics and antiviral agents), analgesic agents, anorexic agents, anti-inflammatory agents, antiepileptic agents, anaesthetic agents, hypnotic agents, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics agents, hormones, nutrients, antiarthritics agents, antiasthmatic agents, anticonvulsants, antihistamines, antinauseants agents, antineoplastic agents, antipruritics agents, antipyretic agents; antispasmodic agents, cardiovascular agents (e.g. calcium channel blockers, beta-blockers, beta-agonists, antiarrhythmic agents, antihypertensive agents, diuretics and vasodilators), central nervous system stimulants; decongestants, hormones, bone growth stimulants, bone resorption inhibitors, immunosuppressive agents, muscle relaxants, psychostimulants, sedatives and tranquilisers. It will be appreciated that this list of therapeutic agents is merely illustrative and should not be considered to be limiting. Many other therapeutic agents are known in the art and may be utilised in a method of the present invention. A detailed description of various therapeutic agents may be found in e.g. Remington's Pharmaceutical Sciences (21st edition, 2005, Mack Publishing Company). The therapeutic agent may exhibit optical isomerism and/or diastereoisomerism. Accordingly, the therapeutic agent may be in the form of a single enantiomer or diastereoisomer, or a mixture (e.g. a racemic mixture) thereof.

In an embodiment, the therapeutic agent has a molecular weight of less than 2000 Daltons, e.g. less than 1500 Daltons, e.g. less than 1000 Daltons, e.g. less than 500 Daltons. In an embodiment, the therapeutic agent is a non-polymeric organic compound having a molecular weight of less than 1000 Daltons, e.g. less than 800 Daltons, e.g. less than 500 Daltons.

In an embodiment, the therapeutic agent is an inhibitor or an activator, e.g. an activator or inhibitor of the membrane protein to which it is bound. In a particular embodiment, the therapeutic agent is a cyclic peptide inhibitor. Examples of cyclic peptide inhibitors include QZ59Se and HT-55. Examples of activators include HT-44 and HT-122.

In an embodiment, the therapeutic agent is an anti-cancer agent. In a particular embodiment, the therapeutic agent is selected from doxorubicin, digoxin, loperamide, berberine, irinotecan, vinblastine, paclitaxel, fexofenadine, cyclosporin, quinidine, tariquidar and verapamil. In an embodiment, the therapeutic agent is cyclosporin A.

Binding of the therapeutic agent to the membrane protein may be via a non-covalent or a covalent interaction. In particular, binding of the therapeutic agent to the membrane protein may be via intermolecular forces such as ionic bonds, hydrogen bonds and van der Waals forces. Binding of the therapeutic agent to the membrane protein may be reversible or irreversible. In an embodiment, the therapeutic agent is bound to the membrane protein via a reversible bond.

The membrane protein-therapeutic agent complex may comprise one or more other components. In one embodiment, the complex further comprises a lipid. Thus, for instance, a method of the present invention may be used to determine whether the presence of a lipid affects binding of the therapeutic agent to the membrane protein. In an embodiment, the complex comprises a nucleotide. In an embodiment, the complex comprises a lipid and a nucleotide.

In an embodiment, the complex does not comprise phosphatidylethanolamine, cardiolipin or another glycerophosholipid. In a particular embodiment, the complex does not comprise a lipid. In an embodiment, the complex does not comprise adenosine diphosphate (ADP), adenosine triphosphate (ATP), or an analogue thereof (e.g. α,β-methyleneadenosine 5'-triphosphate). In an embodiment, the complex does not comprise a nucleotide. In an embodiment, the complex does not comprise tetraphenyl phosphonium.

A micellar solution is formed which comprises a detergent micelle in which the complex is contained. The complex is encapsulated in a micelle for solubilisation, which may at least partially shield the complex during the electrospray ionisation process. Without wishing to be bound by theory, it is believed that the micelle may shield the complex during the droplet phase of the electrospray ionisation process and, moreover, may afford at least partial shielding from ionisation of the complex during this process. The detergent micelle may exert a pressure sufficient to maintain the structure of the membrane protein-therapeutic agent complex, thereby minimising the deleterious effects associated with vaporisation and substantially retaining interactions between the membrane protein and therapeutic agent and interactions within any subunits of the membrane protein. The solution will typically comprise a plurality of micelles containing said complex. The micellar solution may be formed by e.g. incubating the membrane protein with the therapeutic agent in the presence of a detergent.

In an embodiment, the membrane protein is maintained in the detergent micelle in an intact, folded state. This may allow the membrane protein-therapeutic agent complex to be detected in its "native" state. In another embodiment, the membrane protein is present within the detergent micelle in a partially folded or unfolded state.

Preferably, the micellar solution is formed using a non-ionic detergent, as high concentrations of non-ionic detergents can be tolerated more readily during the electrospray process. Suitable non-ionic detergents include n-dodecyl-β-D-maltoside, nonylglucoside, glycosides, neopentyl glycols, polyoxyethylene glycols, facade EM, maltosides, glucosides, and mixtures thereof. Preferably, the detergent comprises n-dodecyl β-D-maltoside and/or nonylglucoside.

In order to minimise dissociation of the membrane protein or precipitation of the complex, the detergent should be present in the micellar solution at a concentration at least equal to, and preferably greater than, the critical micelle concentration (CMC) of the detergent. The critical micelle concentration of the detergent may be determined experimentally using methods known in the art, or it may be obtained from e.g. a textbook, product catalogue or website. For example, the Anatrace products catalogue provides CMC data. Typically, critical micelle concentration values are determined in water at 25° C. Thus, in an embodiment, the solution is an aqueous solution and the detergent is present in the solution at a concentration at least equal to, and preferably greater than, the critical micelle concentration of the detergent in water at 25° C.

In an embodiment, the detergent is present in the micellar solution at a concentration of from about 100 μM to about 100 mM, e.g. from about 100 μM to about 200 μM. In an embodiment, the complex is present in the micellar solution at a concentration of from about 0.1 mg/ml to about 50 mg/ml, e.g. from about 10 mg/ml to about 20 mg/ml.

In an embodiment, the molar ratio of the detergent to the membrane protein is from about 10:1 to 150:1, e.g. from about 30:1 to about 125:1, e.g. from about 50:1 to about 100:1. In a preferred embodiment, the molar ratio of the detergent to the membrane protein is less than or equal to 100:1.

In an embodiment, the micellar solution comprises a molar excess of the therapeutic agent as compared to the membrane protein. In an embodiment, the molar ratio of the therapeutic agent to the membrane protein is at least 2:1, e.g. at least 5:1, e.g. at least 10:1. In an embodiment, the therapeutic agent is present in the micellar solution at a concentration of at least 2 micromolar, e.g. at least 5 micromolar.

The micellar solution may comprise one or more other components, e.g. ammonium acetate. Buffer exchange and concentration of the micellar solution may be achieved using suitable techniques and devices known in the art, e.g. using a Micro Bio-Spin® column (Bio-Rad Laboratories) or a Vivaspin device (GE Healthcare).

The complex is detected using a mass spectrometer comprising a nanoelectrospray ionisation source, a mass analyser and a detector. The mass spectrometer is preferably adapted to transmit and detect ions having mass-to-charge (m/z) ratios in the range of e.g. from about 100 m/z to about 32,000 m/z. Preferably, the mass spectrometer is operated under conditions suitable for maintaining and focusing large macromolecular ions. Preferably, the mass spectrometer is capable of providing a relatively high collisional activation energy to improve the removal detergent micelles. This may improve the resolution of protein peaks, by preventing the mass spectrum from being dominated by peaks attributable to the detergent molecule. By way of illustration, and without limitation, the mass spectrometer may be a Synapt HDMS quadrupole-S2 ion-trap-IM-MS instrument, and more preferably a G2 instrument. The resolution provided by such instruments is particularly suited to resolving peaks generated from a complex comprising a membrane protein bound to a therapeutic agent.

The nanoelectrospray ionisation source is used to vaporise the micellar solution. Nanoelectrospray ionisation is a technique well known in the art (see e.g. Wilm et al, Anal. Chem. 1996, 68, 1-8; and Wilm et al, Int. J. of Mass Spec. and Ion Proc. 1994, 132, 167-180). The use of nanoelectrospray ionisation allows ions, and in particular highly charged ions, to be generated directly from solution. The formation of highly charged ions may allow the detection of high mass complexes at relatively low mass-to-charge (m/z) ratios. The use of a nanoelectrospray ionisation is also desirable from the point of view of allowing the complex, or subunits of the complex, to remain substantially intact. In performing a method of the present invention, it may be preferable to use a nanoflow capillary, e.g. a gold-coated nanoflow capillary, to vaporise the solution.

The micellar solution is vaporised under conditions such that the complex is released from the micelle. The complex may be released from the micelle as a result of collisions between the electrospray and the micelle which serve to disrupt the detergent assembly. Preferably, the vaporisation conditions are selected so that the complex is released from the micelle substantially intact. Preferably, the conditions inside the mass spectrometer are selected to rapidly remove this micelle from the complex containing micelle. Ionisation of the complex may occur during the step of vaporising and/or after release of the complex from the micelle. In some instances, portions of the membrane protein, e.g. hydrophilic/cytoplasmic domains, may become ionised prior to release of the complex from the micelle. Typically, ionisation of the complex occurs during and/or after release of the complex from the micelle. In an embodiment, release and/or ionisation of the complex from the micelle occurs in a collision cell present within the mass spectrometer. Release and/or ionisation of the complex from the micelle may be achieved by adjusting acceleration voltages and/or pressures within the collision cell to remove the detergent while retaining the peaks of the membrane complex.

In an embodiment, the mass spectrometer is operated under one or more of the following conditions: (i) a capillary voltage of from about 0.8 to about 2.2 kV, e.g. from about 1.0 to about 2.0 kV, e.g. from about 1.2 to about 1.8 kV; (ii) a cone voltage of from about 80 to about 240 V, e.g. from about 100 to about 220 V, e.g. from about 120 to about 200 V; (iii) a trap collision energy of from about 80 to about 240 V, e.g. from about 100 to about 220 V, e.g. from about 120 to about 200 V; (iv) a source temperature of from about 0 to about 50° C., e.g. from about 10 to about 30° C., e.g. about 20° C.; (v) a bias voltage of from about 40 to about 200 V, e.g. from about 60 to about 180 V, e.g. from about 80 to about 160 V; and (vi) a backing pressure of from about 1 to about 8 mBar, e.g. from about 3 to about 6 mBar, e.g. from about 4 to about 5 mBar. In a particular embodiment, the mass spectrometer is operated with a bias voltage of from about 40 to about 200 V, e.g. from about 60 to about 180 V, e.g. from about 80 to about 160 V. In a particular embodiment, the trap collision energy is from about 175 to about 200 V.

The ionised complex is then resolved and detected and, if desired, further characterised. In this regard, the present methods are desirable in that ions in which the therapeutic agent is bound to the membrane protein or a fragment thereof can be detected directly using the mass spectrometer, rather than inferred indirectly from mass spectra of the separate components (therapeutic agent and protein). Moreover, where the micellar solution or the complex comprises one or more additional components, e.g. one or more components selected from lipids and nucleotides, the binding of one or more of said components to the membrane protein may be detected simultaneously. For instance, the method may comprise detecting a plurality of ions selected from the group consisting of ions containing the therapeutic agent bound to the membrane protein or a fragment thereof, ions containing one or more additional components (e.g. selected from lipid and nucleotides) bound to the membrane protein or a fragment thereof, and ions in which the therapeutic agent and one or more additional components are bound to the membrane protein or a fragment thereof. Thus, the present methods may be used to detect concomitant binding of the membrane protein with the therapeutic agent and one or more other species which compete for binding sites.

In a particular embodiment, the complex is detected using ion mobility-mass spectrometry (IM-MS). The use of IM-MS may allow the stoichiometry of therapeutic agent binding, and the overall effects of therapeutic agent binding on the dynamics, stabilities, oligomeric structures and conformations of membrane proteins, to be determined. For instance, the stoichiometry and oligomeric structure of complexes may be characterised by assessing mass differences. As a further example, dynamics, stabilities and conformations may be characterised by changes in charge states or by differences in arrival time distributions (i.e. ion mobility).

The following non-limiting Examples illustrate the present invention.

EXAMPLE 1

MS and IM-MS data of a membrane transporter, P-gp, binding to different drugs were acquired. The drugs included: two stereoisomers of a cyclic peptide inhibitor (QZ59Se, SSS; and QZ59Se, RRR); a further inhibitor (HT-55); and two activators (HT-35 and HT-122).

P-glycoprotein (P-gp) was expressed and purified as reported previously (Aller et al, Science, 2009, 323, 1718-1722). In this method, P-gp was expressed in *P. pastoris* strain and purified as a his-tagged protein from the membranes solubilised with Triton X-100. Buffer was exchanged by washing with buffer containing 20 mM imidazole, 0.04% sodium cholate and 0.0675% β-DDM. The protein was concentrated, subjected to gel filtration chromatography and assayed for purity by SDS-PAGE.

An aliquot (30 µl) of mouse P-gp solution (9 mg/ml) in 0.07% β-DDM, 0.04% sodium cholate, 100 mM NaCl, 0.2 mM TCEP, 20 mM Hepes, pH 7.5 was buffer-exchanged using a membrane filter and diluted 3-fold in 300 mM ammonium acetate, pH 7.5. Spectra of P-gp with drug compounds were obtained by first pre-incubating 2-3 mg/ml P-gp protein with 1-10 molar equivalents of the test compound for 15 minutes to overnight prior to nanoelectrospray ionisation mass spectrometry.

Mass spectrometry measurements were carried out on a Synapt HDMS (Waters, Manchester, UK) quadrupole-S2 ion-trap-IM-MS instrument modified for transmission and detection of ions at high m/z ratios. Aliquots of complex-containing solutions (2 µL) in detergent were introduced via gold-coated nanoflow electrospray capillaries. Instrument parameters were optimised to remove detergents while preserving non-covalent interactions between small molecules and membrane protein. The MS conditions were: capillary voltage, 1.2-1.8 kV; cone voltage, 120-200 V; trap collision energy, 120-200 V; source temperature, 20° C.; bias voltage, 80-160 V; and backing pressure, 4-5 mBar.

Using this protocol, the stoichiometries of both drug and nucleotide binding to this transporter were determined. FIG. 1 shows the mass spectra of: (A) apo-P-gP; (B) P-gp bound to the inhibitor QZ59Se, RRR; (C) P-gp bound to the inhibitor HT-35; and (D) P-gp bound to the activator HT-122. It can be seen that binding of the different drugs to P-gp altered the mass spectrum of the membrane protein, revealing that a drastic conformational change occurs upon binding of the protein to the drugs.

EXAMPLE 2

A similar experiment was performed to detect binding between cyclosporin A and P-gp. Cyclosporin A (CsA; 1202.6 Da) is an immunosuppressant and antifungal antibiotic known to inhibit P-gp ATPase activity with an $IC_{50}$ of 3.4 µM. In addition, the concomitant binding of nucleotides, lipid and CsA to P-gp was also detected.

Materials and Methods

His-tagged P-glycoprotein was expressed in *P.pastoris* and purified according to a protocol described previously (see Aller et al, supra). Lipids were purchased from Avanti Polar Lipids. Cyclosporin A, ammonium acetate, ATP and ATPγS were purchased from Sigma-Aldrich.

Before analysis, P-gp was buffer exchanged into 200 mM ammonium acetate pH 7 supplemented with 0.02% n-dodecyl-β-D-maltoside (DDM), using micro BioSpin-6 devices (Bio-Rad). Lipids were first prepared at 2 mM in chloroform and then diluted to 20 μM in 200 mM ammonium acetate pH 7 supplemented with 0.02% DDM. Cyclosporin was first dissolved at 8 mM in methanol and then diluted to 5-100 μM in 200 mM ammonium acetate pH 7 supplemented with 0.02% DDM. MS spectra were acquired on a Q-TOF2 (Micromass) modified for the transmission and detection of high mass complexes. Samples were introduced in the ion-source via gold-coated nanoflow capillaries. Capillary, cone and extractor voltages were set at 1.5 kV, 175-200 V and 5 V, respectively. Micelle transmission was enhanced by increasing the Pirani pressure to 30 mbar. P-gp was dissociated from the micelle with a collision energy of 175-200 V and 10 psi of argon. Spectra were analysed with Massign software.

Results

Figure 2A:
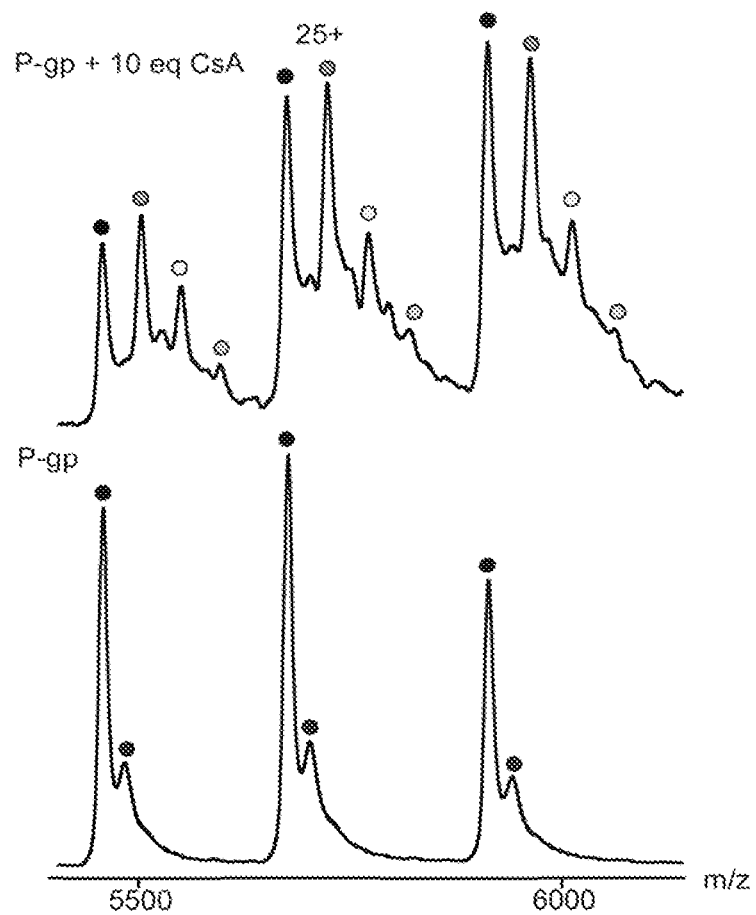
FIG. 2 shows: (a) native mass spectra obtained before (bottom) and after (top) 5 min incubation with 10 equivalents of CsA (the black dots denote the apo P-gp, while the binding of co-purified DDM and the binding of the first, second and third CsA are denoted by shaded dots; (b) equilibrium titration of CsA (the inset shows the structure of CsA; the apo P-gp is plotted as the uppermost line, while the first, second and third adducts are plotted as the second highest, third highest and lowermost lines respectively); and (c) native mass spectra of P-gp incubated with 1 mM $MgCl_2$ plus 50 µM ATP (top) or 50 µM ATPγS (bottom) (the shaded squares denote the binding of the first and second nucleotides).
Figure 2B:
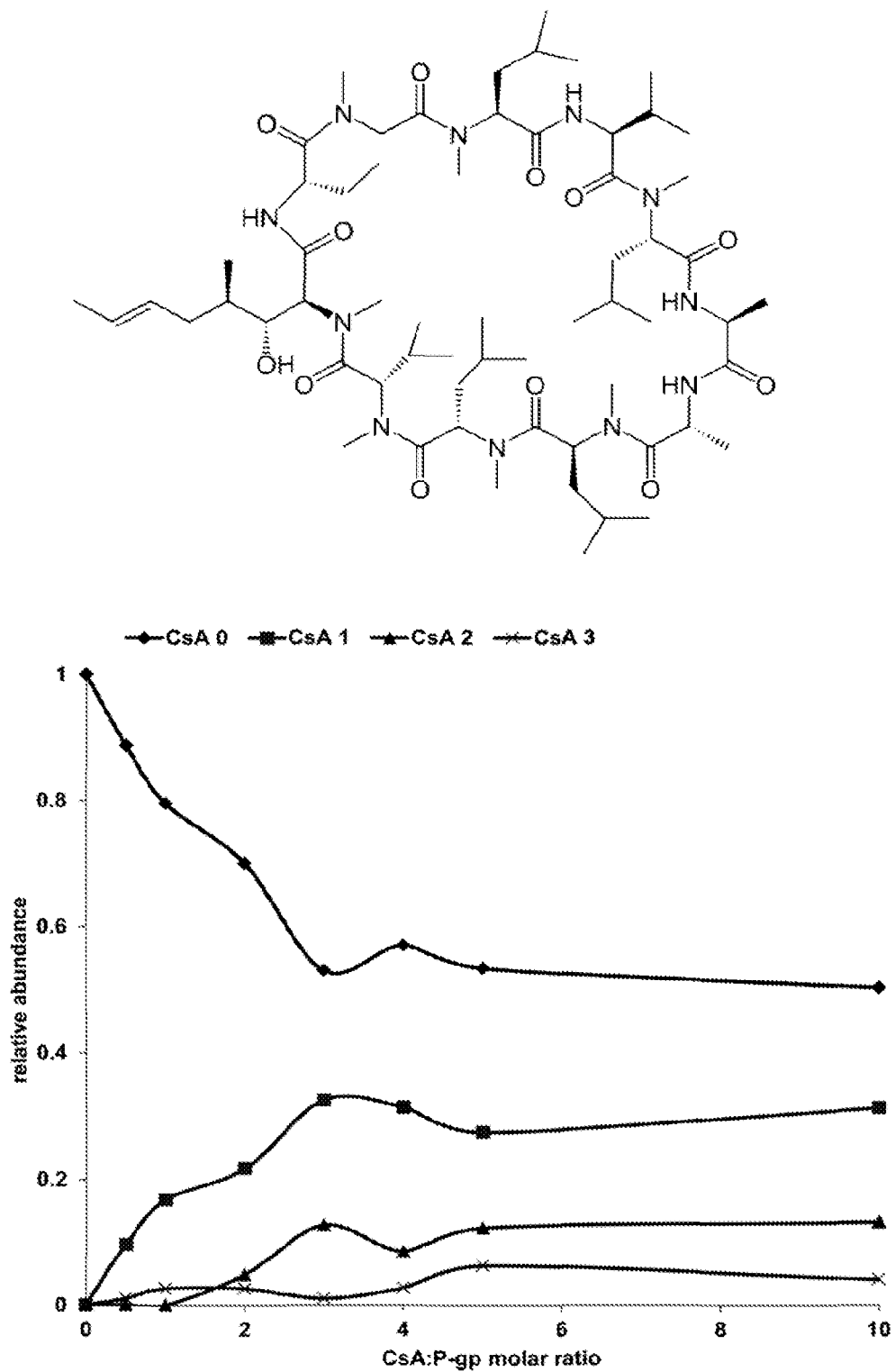
Figure 2C:
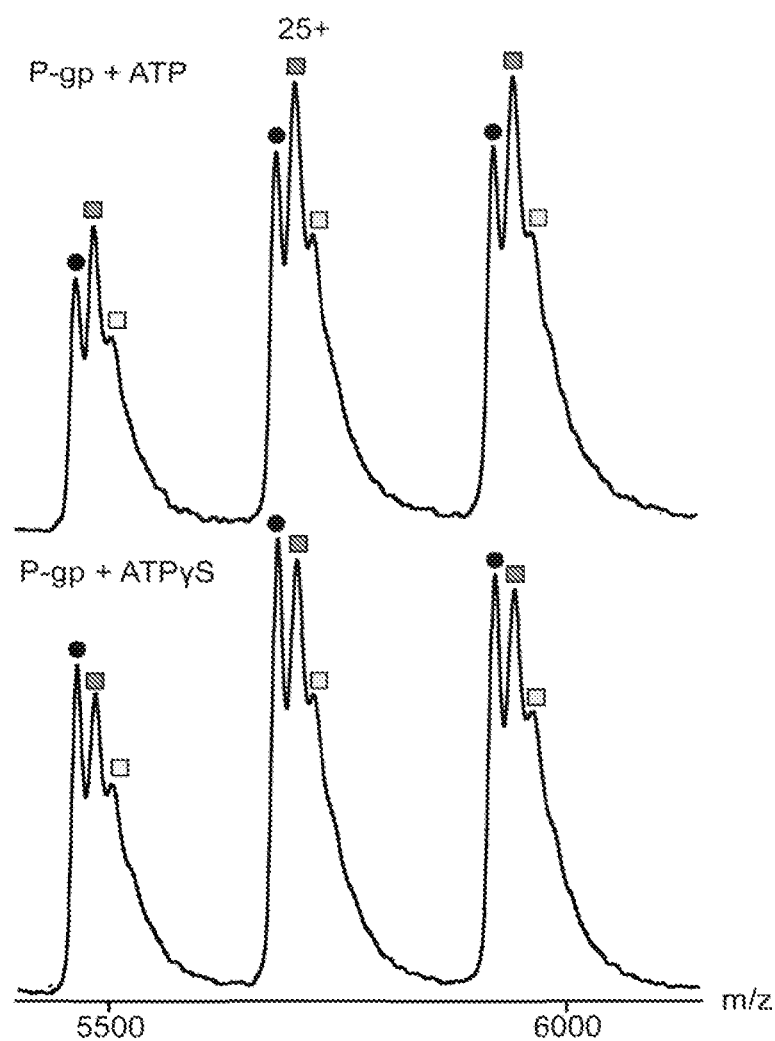

With reference to FIG. 2, native mass spectra of P-gp reveal a broad distribution of charge states which is consistent with the open-inward conformation in which a large proportion of the surface is exposed. Despite the high collision energy used to release the membrane protein from the micelle, an adduct is clearly visible at +550 Da corresponding to some co-purified n-dodecyl-β-D-maltoside (FIG. 2a). Following incubation of P-gp with an excess of CsA, up to three additional series of charge states appeared, corresponding to three CsA adducts (FIG. 2a). At low collision energies, it the intensity of the CsA adducts was found to depend on the concentration of the drug (FIG. 2b). It could also be seen that P-gp is bound to one or two ATP/ATPγS (FIG. 2c).

Figure 3A:
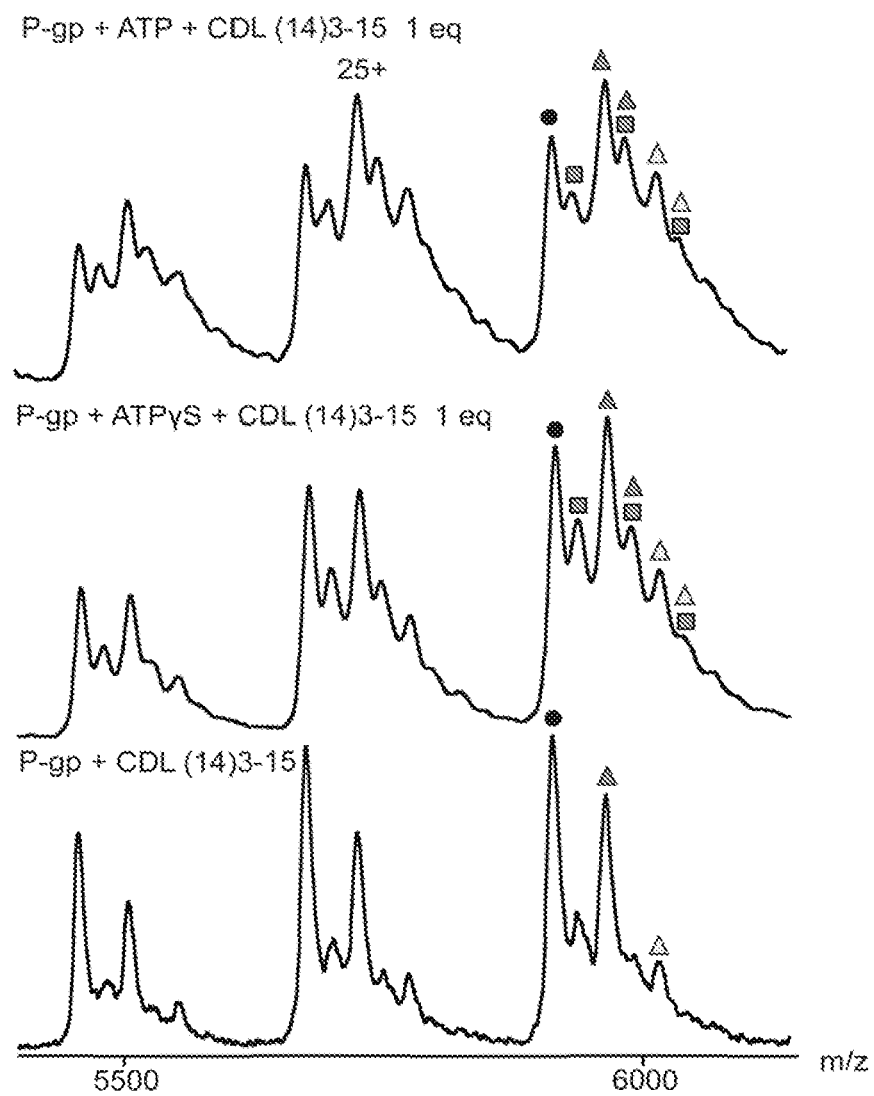
FIG. 3 shows: (a) binding of CDL 14:1(3)-15:1 on an ATP or ATPγS bound P-gp; (b) binding of CsA on an ATP or ATPγS bound P-gp; and (c) spectra obtained after 20 min incubation of P-gp with 5 equivalents of CsA followed by 20 min incubation with 2 equivalents of CDL 14:1(3)-15:1 (top) and vice-versa (bottom). Apo P-gp is represented by black dots, while the first, second and third adducts are represented by shaded dots. CsA, nucleotides and cardiolipin 14:1(3)-15:1 are represented by shaded dots, squares and triangles, respectively.
Figure 3B:
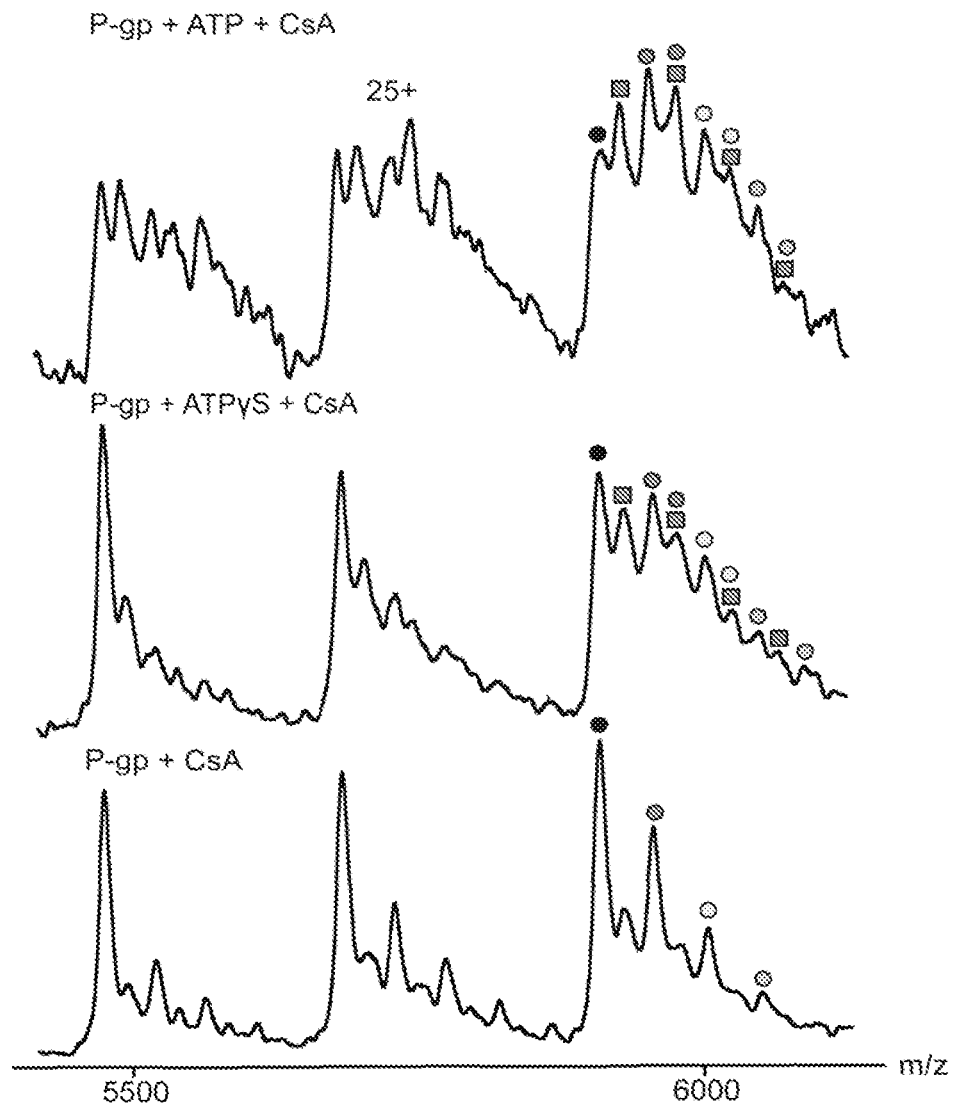
Figure 3C:
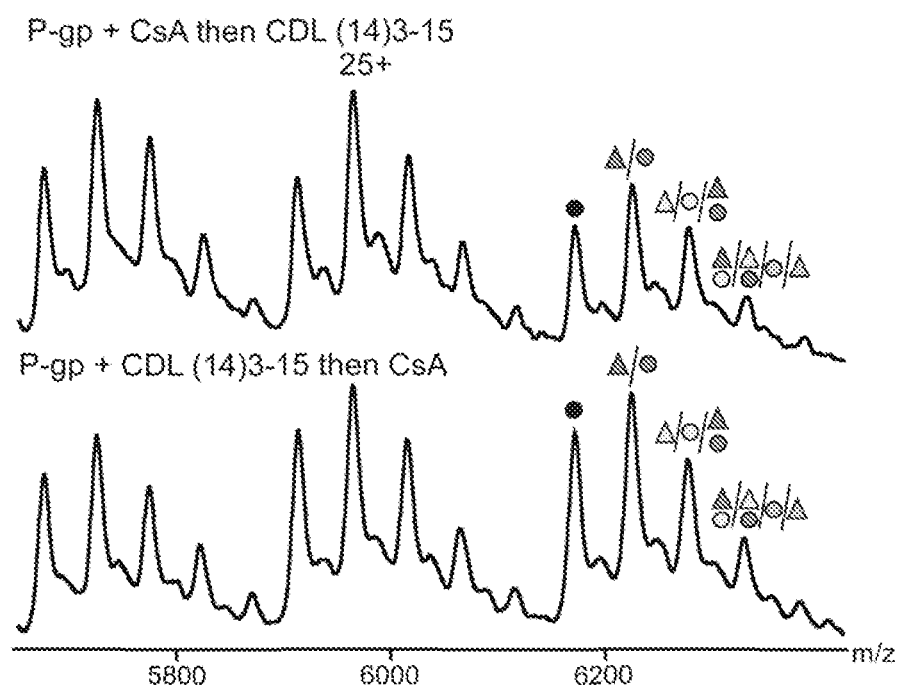

In order to obtain more insight into P-gp specificity and its catalytical cycle, experiments were conducted in which samples were first incubated with ATP or ATPγS and then incubated with cardiolipin 14:1(3)-15:1 or CsA. The results of these experiments are presented in FIG. 3. The mixed species containing nucleotides and cardiolipin or CsA could be readily identified (FIGS. 3a and b). More specifically, it was possible to separate species bound to one ATP or ATPγS and one or two molecules of cardiolipin or CsA. These data also suggest that P-gp is able to bind to CsA and the short chain cardiolipin at the same time (FIG. 3c), regardless of which one is incubated first.

The invention claimed is:

1. A method of detecting a complex comprising a membrane protein bound to a therapeutic agent by mass spectrometry, wherein the method comprises:
 (a) providing a solution comprising a detergent micelle in which said complex is contained, wherein the detergent is present in the solution at a concentration which is greater than or equal to the critical micelle concentration of the detergent, and wherein the solution comprises a mass spectrometry compatible buffer;
 (b) providing a mass spectrometer comprising a nanoelectrospray ionisation source, a mass analyser and a detector;
 (c) vaporising the solution using the nanoelectrospray ionisation source under conditions such that the complex is released from the micelle;
 (d) ionising the complex;
 (e) resolving the ionised complex using the mass analyser; and
 (f) detecting the resolved complex using the detector, wherein the mass spectrometer is operated under one or more of the following conditions: (i) the capillary voltage of the nanoelectrospray ionisation source is from about 0.8 to about 2.2 kV; (ii) the cone voltage of the nanoelectrospray ionisation source is from about 80 to about 240 V; (iii) the trap collision energy is from about 80 to about 240 V; (iv) the source temperature is from about 0 to about 50° C.; (v) the bias voltage is from about 40 to about 200 V; and (vi) the backing pressure is from about 1 to about 8 mBar.

2. A method according to claim 1, wherein the membrane protein is an integral membrane protein.

3. A method according to claim 2, wherein the integral membrane protein is a G protein-coupled receptor, a membrane transporter, an ATP-binding cassette transporter or a proton driven transporter.

4. A method according to claim 1, wherein the membrane protein is selected from EmrE, LmrP, MscL, BtuCD, BtuC$_2$D$_2$, LmrCD, MacB, MexB, P-gp, MsbA, NorM and KirBac3.1.

5. A method according to claim 1, wherein the therapeutic agent is a drug.

6. A method according to claim 1, wherein the therapeutic agent is a non-polymeric organic compound having a molecular weight of less than 1000 Daltons.

7. A method according to claim 1, wherein the therapeutic agent is an inhibitor or an activator.

8. A method according to claim 7, wherein the therapeutic agent is a cyclic peptide inhibitor.

9. A method according to claim 1, wherein the complex further comprises a lipid and/or a nucleotide.

10. A method according to claim 1, wherein the solution comprises a non-ionic detergent.

11. A method according to claim 10, wherein the solution comprises n-dodecyl-β-D-maltoside and/or nonylglucoside.

12. A method according to claim 1, wherein the solution is an aqueous solution.

13. A method according to claim 1, wherein the molar ratio of the detergent to the membrane protein in the solution is from about 10:1 to about 150:1.

14. A method according to claim 1, wherein the solution is sprayed using a gold-coated nanoflow capillary.

15. A method according to claim 1, wherein the complex is released from the micelle substantially intact.

16. A method according to claim 1, wherein the mass spectrometer comprises a collision cell in which release and/or ionisation of the complex takes place.

17. A method according to claim 1, wherein the mass spectrometer is operated with a bias voltage of from about 40 to about 200 V.

18. A method according to claim 1, wherein the complex is detected by ion mobility-mass spectrometry.

19. A method according to claim 1, wherein the structure or conformation of the complex is characterised.

20. A method according to claim 1, wherein the mass spectrometer is operated with a bias voltage of from about 60 to about 180 V.

21. A method according to claim 1, wherein the mass spectrometer is operated with a bias voltage of from about 80 to about 160 V.

* * * * *